(12) United States Patent
Raab et al.

(10) Patent No.: US 10,493,208 B2
(45) Date of Patent: Dec. 3, 2019

(54) DRIVE MECHANISM FOR A MEDICATION DELIVERY DEVICE AND MEDICATION DELIVERY DEVICE

(71) Applicant: SANOFI-AVENTIS DEUTSCHLAND GMBH, Frankfurt am Main (DE)

(72) Inventors: Steffen Raab, Frankfurt am Main (DE); Ulrich Bruggemann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 99 days.

(21) Appl. No.: 15/902,600

(22) Filed: Feb. 22, 2018

(65) Prior Publication Data
US 2018/0177948 A1 Jun. 28, 2018

Related U.S. Application Data

(63) Continuation of application No. 15/667,687, filed on Aug. 3, 2017, now Pat. No. 10,232,119, which is a
(Continued)

(51) Int. Cl.
*A61M 5/315* (2006.01)
*A61M 5/24* (2006.01)
(Continued)

(52) U.S. Cl.
CPC .......... *A61M 5/31501* (2013.01); *A61M 5/24* (2013.01); *A61M 5/3148* (2013.01);
(Continued)

(58) Field of Classification Search
CPC .. A61M 5/31501; A61M 5/24; A61M 5/3148; A61M 5/31543; A61M 5/31551;
(Continued)

(56) References Cited

U.S. PATENT DOCUMENTS 533,575 A 2/1895 Wilkens
1,718,596 A 6/1929 Smith
(Continued)

FOREIGN PATENT DOCUMENTS

AU 2009324405 B2 10/2014
CA 2138528 12/1998
(Continued)

OTHER PUBLICATIONS

"Pen-injectors for medical use—Part 1: Pen-injectors—Requirements and test methods," International Standard, reference number: ISO 11608-1:2000(E), first edition Dec. 15, 2000, 32 pages.
(Continued)

*Primary Examiner* — Edelmira Bosques
(74) *Attorney, Agent, or Firm* — Fish & Richardson P.C.

(57) ABSTRACT

A drive mechanism for a medication delivery device is presented having a housing, a rotation member that rotates in a first direction with respect to the housing during setting of a dose of a medication and rotates in a second direction with respect to the housing during delivery of the dose, the second direction being opposite to the first direction. The device also has a piston rod that is displaced in a distal direction with respect to the housing for delivering the dose, a drive member which follows rotational movement of the rotation member in the second direction during delivery of the dose, and a stop member which prevents rotational movement of the drive member with respect to the housing in the first direction during setting of the dose.

9 Claims, 14 Drawing Sheets

Related U.S. Application Data continuation of application No. 14/459,440, filed on Aug. 14, 2014, now Pat. No. 9,750,888, which is a continuation of application No. 12/333,459, filed on Dec. 12, 2008, now Pat. No. 8,840,591.

(51) Int. Cl.
  *A61M 5/31* (2006.01)
  *F16H 25/12* (2006.01)

(52) U.S. Cl.
  CPC ...... *A61M 5/3158* (2013.01); *A61M 5/31543* (2013.01); *A61M 5/31551* (2013.01); *A61M 5/31555* (2013.01); *A61M 5/31581* (2013.01); *A61M 5/31585* (2013.01); *A61M 5/31593* (2013.01); *F16H 25/12* (2013.01); *A61M 5/3156* (2013.01); *A61M 5/3157* (2013.01); *A61M 5/31511* (2013.01); *A61M 5/31515* (2013.01); *A61M 5/31535* (2013.01); *A61M 5/31536* (2013.01); *A61M 5/31541* (2013.01); *A61M 5/31556* (2013.01); *A61M 5/31558* (2013.01); *A61M 5/31561* (2013.01); *A61M 5/31575* (2013.01); *A61M 2005/2407* (2013.01); *A61M 2005/3125* (2013.01); *A61M 2005/3126* (2013.01); *A61M 2005/3152* (2013.01); *A61M 2205/581* (2013.01); *A61M 2205/582* (2013.01); *Y10T 74/18568* (2015.01); *Y10T 74/18696* (2015.01)

(58) Field of Classification Search
  CPC .......... A61M 5/31555; A61M 5/31581; A61M 5/31585; A61M 5/31593
  See application file for complete search history.

(56) References Cited

U.S. PATENT DOCUMENTS

| | | | |
|---|---|---|---|
| 2,653,604 A | 9/1953 | Hein, Jr. | |
| 4,465,478 A | 8/1984 | Sabelman et al. | |
| 4,592,745 A | 6/1986 | Rex et al. | |
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,827,232 A | 10/1998 | Chanoch et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giamballista et al. | |
| 6,936,032 B1 | 8/2005 | Bush, Jr. et al. | |
| 7,104,972 B2 | 9/2006 | Moller et al. | |
| 7,112,187 B2 | 9/2006 | Karlsson | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,187,233 B2 | 5/2012 | Harms et al. | |
| 8,827,232 B2 | 9/2014 | Crowley | |
| 8,840,591 B2 | 9/2014 | Raab et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0068236 A1 | 4/2004 | Moller et al. | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0165363 A1 | 7/2005 | Judson et al. | |
| 2006/0153693 A1 | 7/2006 | Fiechter et al. | |
| 2007/0016143 A1 | 1/2007 | Miller et al. | |
| 2007/0123829 A1 | 5/2007 | Atterbury et al. | |
| 2008/0027397 A1 | 1/2008 | DeRuntz et al. | |
| 2008/0108769 A1 | 5/2008 | Kanega et al. | |
| 2009/0275916 A1 | 11/2009 | Harms et al. | |

FOREIGN PATENT DOCUMENTS

| | | |
|---|---|---|
| CA | 2359375 | 7/2000 |
| CN | 1243578 | 2/2000 |
| CN | 1889990 | 1/2007 |
| CN | 101094699 A | 12/2007 |
| CN | 101262899 | 9/2008 |
| CN | 201324413 | 10/2009 |
| DE | 102005060929 A1 | 3/2007 |
| EP | 0496141 | 7/1992 |
| EP | 0897729 | 2/1999 |
| EP | 0937471 A2 | 8/1999 |
| EP | 0937476 A2 | 8/1999 |
| EP | 1250167 B1 | 7/2005 |
| EP | 1681070 A1 | 7/2006 |
| EP | 1353712 B1 | 10/2006 |
| EP | 1776975 | 4/2007 |
| EP | 1923085 A1 | 5/2008 |
| EP | 1974761 A2 | 10/2008 |
| JP | H08-730 A | 1/1996 |
| JP | H08-510392 A | 11/1996 |
| RU | 2214286 C2 | 10/2003 |
| WO | 93/07922 A1 | 4/1993 |
| WO | WO 03/24160 | 12/1993 |
| WO | WO 98/57688 | 12/1998 |
| WO | 99/38554 A1 | 8/1999 |
| WO | 01/10484 A1 | 2/2001 |
| WO | 01/72361 A1 | 10/2001 |
| WO | 02/30495 A2 | 4/2002 |
| WO | WO 02/092153 | 11/2002 |
| WO | 03/080160 A1 | 10/2003 |
| WO | WO 2005/018721 | 3/2005 |
| WO | WO 2005/053778 | 6/2005 |
| WO | 2006/084876 A1 | 8/2006 |
| WO | WO 2007/030957 | 3/2007 |
| WO | WO 2008/058666 | 5/2008 |
| WO | 2008/138908 A1 | 11/2008 |
| WO | 2010/06796 A1 | 6/2010 |

OTHER PUBLICATIONS

Australian Examination Report for AU App. No. 2009324405, dated May 2, 2014.

European Search Report for EP App. No. 08021628, dated Apr. 27, 2009.

European Search Report for EP App. No. 15153930, completed Jul. 6, 2015.

Decision of Grant for RU App. No. 2011128680, dated Jan. 29, 2014.

International Search Report and Written Opinion for Int. App. No. PCT/EP2009/066742, dated Apr. 6, 2010.

(56) References Cited

OTHER PUBLICATIONS

Japanese Office Action for JP App. No. 2011-540078, dated Nov. 12, 2013.
Russian Office Action for RU App. No. 2011128680, dated Sep. 23, 2011.
Malaysian Examination Report for MY App. No. PI 2011002316, dated Oct. 15, 2014.
Mexican Office Action for MX App. No. MX/a/2011/005879, dated Feb. 27, 2014.
Chinese Office Action for CN App. No. 200980154662.1, dated Jan. 4, 2013.
International Preliminary Report on Patentability in International Application No. PCT/EP2009/066742, dated Jun. 14, 2011, 7 pages.

DRIVE MECHANISM FOR A MEDICATION DELIVERY DEVICE AND MEDICATION DELIVERY DEVICE

CROSS REFERENCE TO RELATED APPLICATIONS

The present application is a continuation of U.S. patent application Ser. No. 15/667,687, filed Aug. 3, 2017, which is a continuation of U.S. patent application Ser. No. 14/459,440, filed Aug. 14, 2014, now U.S. Pat. No. 9,750,888, which is a continuation of U.S. patent application Ser. No. 12/333,459, filed Dec. 12, 2008, now U.S. Pat. No. 8,840,591. The entire disclosure contents of these applications are herewith incorporated by reference into the present application.

FIELD OF THE INVENTION

The present invention relates to a drive mechanism for a medication delivery device and a medication delivery device incorporating such a drive mechanism.

BACKGROUND

In a medication delivery device, a piston within a cartridge that contains medication may be displaced with respect to the cartridge in the distal direction by a piston rod which moves in the distal direction with respect to the cartridge. Thereby, a dose of medication can be expelled from the cartridge. A medication delivery device is described in US 2007/0123829 A1, for example.

It is often desirable that the actually delivered dose of medication matches the dose which was previously set for injection by a user or which the device was designed to deliver as close as possible, i.e. dose accuracy should be good.

It is an object to provide for a drive mechanism that facilitates provision of an improved medication delivery device, for example a device with good dose accuracy. Furthermore, an improved medication delivery device should be provided for.

This object may be achieved by a drive mechanism according to the independent claim. Further features, advantages and expediencies are subject matter of the dependent claims.

SUMMARY

According to one aspect, a drive mechanism for a medication delivery device comprises a housing having a proximal end and a distal end, a rotation member which is adapted to be rotated in a first direction with respect to the housing during setting of a dose of a medication and to be rotated in a second direction with respect to the housing during delivery of the dose, the second direction being opposite to the first direction. Furthermore, the drive mechanism comprises a piston rod which is adapted to be displaced in a distal direction with respect to the housing for delivering the dose, a drive member which follows rotational movement of the rotation member in the second direction during delivery of the dose, and a stop member which prevents rotational movement of the drive member with respect to the housing in the first direction during setting of the dose, wherein the rotational movement of the drive member in the second direction is converted into movement of the piston rod in the distal direction with respect to the housing.

Mechanical interaction of stop member and drive member, for example, interlocking, engagement and/or abutment, during rotation of the rotation member in the first direction may prevent rotational movement of the drive member with respect to the housing in the first direction and, in particular, with respect to the stop member during setting of the dose. Thus, rotation of the drive member during dose setting can be avoided. The drive member may be coupled to the piston rod so as to convert its rotational movement in the second direction into distal movement of the piston rod with respect to the housing. The drive member may (also) be coupled to the piston rod so as to convert its rotational movement in the first direction with respect to the housing into proximal movement of the piston rod with respect to the housing. Accordingly, the risk of the piston rod being moved in the proximal direction during dose setting can be reduced by preventing rotational movement of the drive member in the first direction during setting of the dose due to provision of the stop member. Unintentional proximal movement of the piston rod may result in decreased dose accuracy. Consequently, dose accuracy may be improved by preventing (any) rotation of the drive member with respect to the housing during dose setting.

According to a preferred embodiment, the drive member and the rotation member are rotatable around a common rotation axis.

According to another preferred embodiment, the piston rod is displaced in the distal direction with respect to the housing along the rotation axis. The rotation axis may run along the piston rod and, in particular, along a main direction of extent of the piston rod.

According to another preferred embodiment, the piston rod is displaced in the distal direction with respect to the housing transversally with respect to the rotation axis. The rotation axis may, in particular, run transversally, for example perpendicularly, with respect to a displacement axis along which the piston rod is displaced in the distal direction with respect to the housing and, in particular, with respect to the drive member. The displacement axis may run along the piston rod and, in particular, along a main direction of extent of the piston rod.

According to another preferred embodiment, the drive mechanism comprises a dose member. The dose member is preferably movable with respect to the housing during setting and/or delivery of the dose. The dose member may be movable in the proximal direction with respect to the housing for setting the dose. The dose member may be movable in the distal direction with respect to the housing for delivering the set dose. Movement of the dose member with respect to the housing may be converted into rotational movement of the rotation member with respect to the housing. Movement of the dose member for setting the dose may be converted into rotational movement of the rotation member with respect to the housing in the first direction. Movement of the dose member for delivering the set dose may be converted into rotational movement of the rotation member with respect to the housing in the second direction. The dose member may be secured against rotational movement with respect to the housing. The dose member may be splined to the housing, for example. The dose member may be movable with respect to the rotation member. Movement of the dose member with respect to the rotation member may be converted into rotational movement of the rotation member.

According to another preferred embodiment, the dose member and the rotation member are engaged, preferably threadedly engaged and/or permanently engaged. Rotational movement of the rotation member may be achieved by the (threaded) engagement which may convert (linear) movement of the dose member into rotational movement of the rotation member with respect to the housing.

According to another preferred embodiment, the dose member and the rotation member are coupled to one another via or (immediately) by a lever. The lever may be pivotally around the rotation axis during movement of the dose member for setting and/or delivery of the dose. The lever may be pivotally around the rotation axis in the first direction during movement of the dose member for setting of the dose. The lever may be pivotally around the rotation axis in the second direction during movement of the dose member for delivering the dose.

According to another preferred embodiment, the drive member, preferably permanently, abuts and/or engages one of or both of stop member and rotation member during (rotational) movement of the rotation member for setting and delivery of the dose. The drive member may be coupled to stop member and/or rotation member during setting and delivery of the dose.

According to another preferred embodiment, the drive member is arranged between stop member and rotation member.

According to another preferred embodiment, the rotation member and the drive member and/or the stop member and the drive member are held in abutment by a force provided by a resilient member, in particular a spring member, during setting and delivery of the dose, in particular during rotational movement of the rotation member in the first direction and in the second direction. Preferably, the rotation member and the stop member are held in abutment with the drive member by the force provided by the spring member during setting and delivery of the dose.

According to another preferred embodiment, the drive member and the rotation member are coupled, preferably permanently, to one another by a (first) uni-directional friction clutch mechanism. This friction clutch mechanism may be configured to permit relative rotational movement between rotation member and drive member during movement of the rotation member for setting of the dose and to prevent relative rotational movement of rotation member and drive member during movement of the rotation member for delivery of the dose.

According to another preferred embodiment, the drive member and the stop member are coupled, preferably permanently, to one another by a (second) uni-directional friction clutch mechanism. This friction clutch mechanism may be configured to prevent relative rotational movement between stop member and drive member during movement of the rotation member for setting of the dose and to permit relative rotational movement of stop member and drive member during movement of the rotation member for delivery of the dose.

According to another preferred embodiment, the stop member is secured against rotational movement with respect to the housing.

According to another preferred embodiment, the stop member is (linearly) displaceable with respect to the housing, preferably without rotating. The stop member may be displaceable along the rotation axis with respect to the housing. The rotation member may be secured against displacement with respect to the housing. Alternatively, the rotation member is displaceable with respect to the housing. Rotation member and stop member may be displaceable with respect to the housing.

Alternatively, the stop member may be secured against rotation and displacement with respect to the housing. The rotation member may be displaceable with respect to the housing, in this case.

According to another preferred embodiment, the spring member abuts the stop member or is integrated in the stop member.

According to another preferred embodiment, the drive member, the stop member, the rotation member and/or the dose member may be formed as or may comprise a sleeve. A rod, for example the piston rod or an axis rod which defines the rotation axis may extend through one of, more of or all of drive sleeve, stop sleeve, rotation sleeve and dose sleeve.

According to another preferred embodiment, the drive member engages the piston rod.

According to another preferred embodiment, the drive member is splined to the piston rod.

According to another preferred embodiment, the rotational movement of the drive member in the second direction is converted into rotational movement of the piston rod with respect to the housing, in particular rotational movement in the same direction and/or by the same angle, and movement of the piston rod with respect to the housing in the distal direction. The piston rod may be threadedly coupled to the housing, in particular threadedly engaged with the housing, for this purpose.

According to another preferred embodiment, the rotational movement of the drive member is converted into pure linear movement of the piston rod in the distal direction, Accordingly, the piston rod may be moved in the distal direction without rotating with respect to the housing. It is particularly suitable for the drive member to comprise (radial) gear teeth for engaging the piston rod, for this purpose.

Another aspect relates to a medication delivery device that comprises a drive mechanism as described above. The device furthermore comprises a cartridge that comprises a plurality of doses of a medication. A piston may be arranged within the cartridge, the piston being displaceable in the distal direction with respect to the cartridge for delivering a dose of medication from the cartridge. The piston rod may be arranged to drive the piston in the distal direction with respect to the cartridge. The cartridge may be attached, permanently or releasably, to the housing.

Features which are described herein above and below in connection with the drive mechanism may also be applied for the corresponding medication delivery device and vice versa.

Further features, refinements and expediencies become apparent from the following description of the exemplary embodiments in connection with the figures.

BRIEF DESCRIPTION OF THE FIGURES

Like elements, elements of the same kind and identically acting elements are provided with the same reference numerals in the figures.

DETAILED DESCRIPTION

Figure 1:
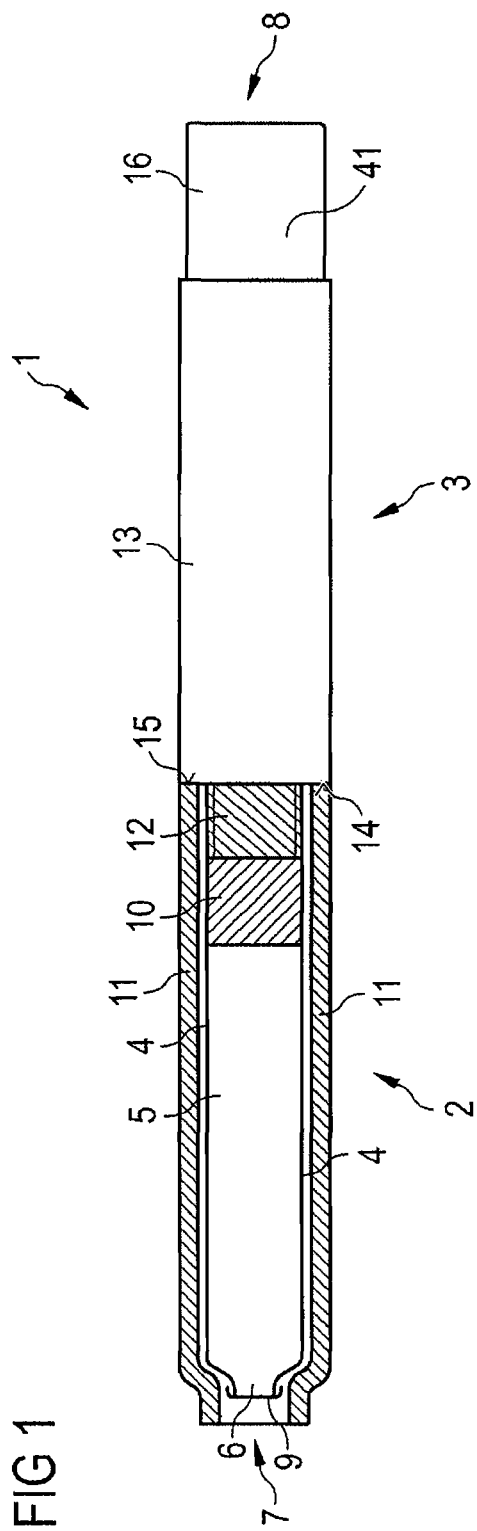
FIG. 1 schematically shows a partly sectional side view of an exemplary embodiment of a medication delivery device.
Figure 2:
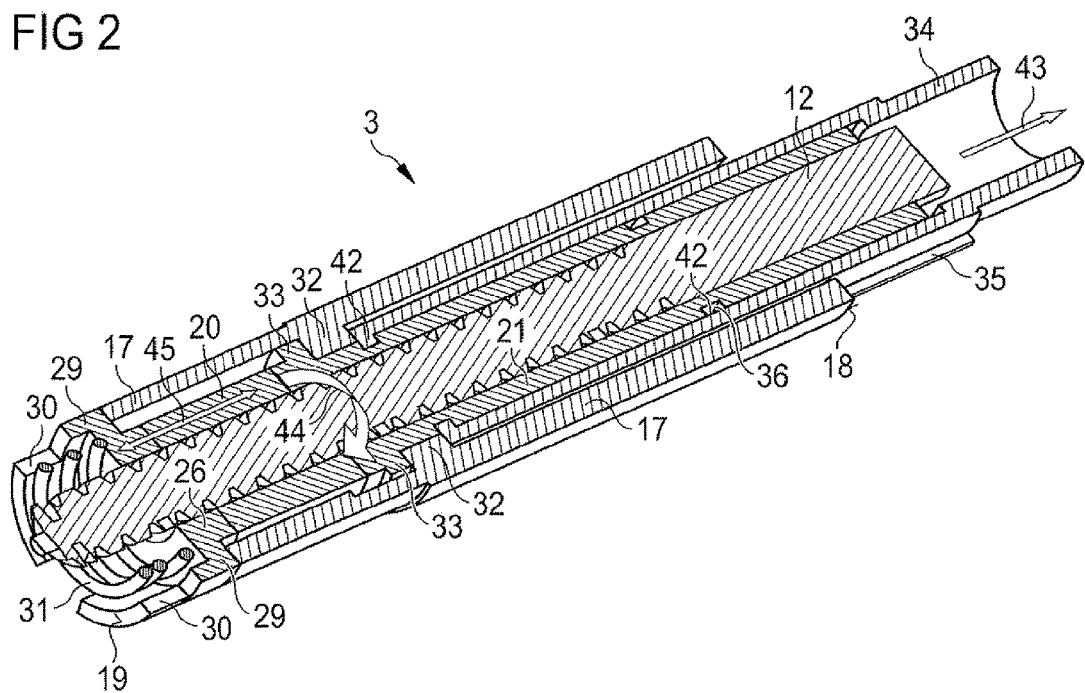
FIG. 2 schematically shows a perspective sectional view of a part of a drive mechanism according to a first embodiment with schematically indicated movements of elements thereof during setting of a dose.
Figure 3:
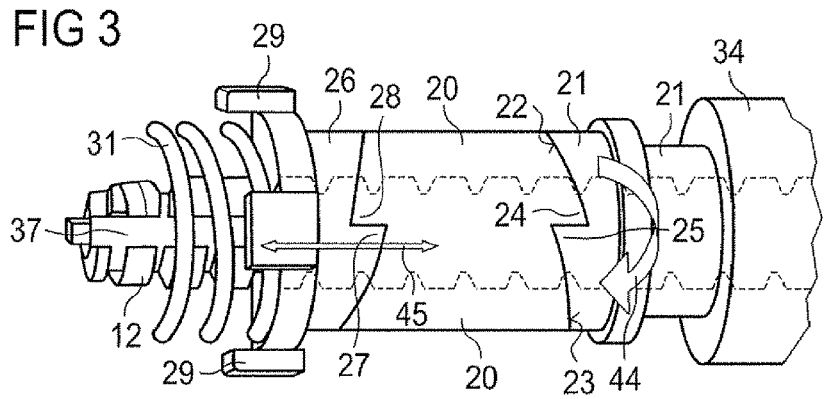
FIG. 3 schematically shows a more detailed side view of a part of FIG. 2.
Figure 4:
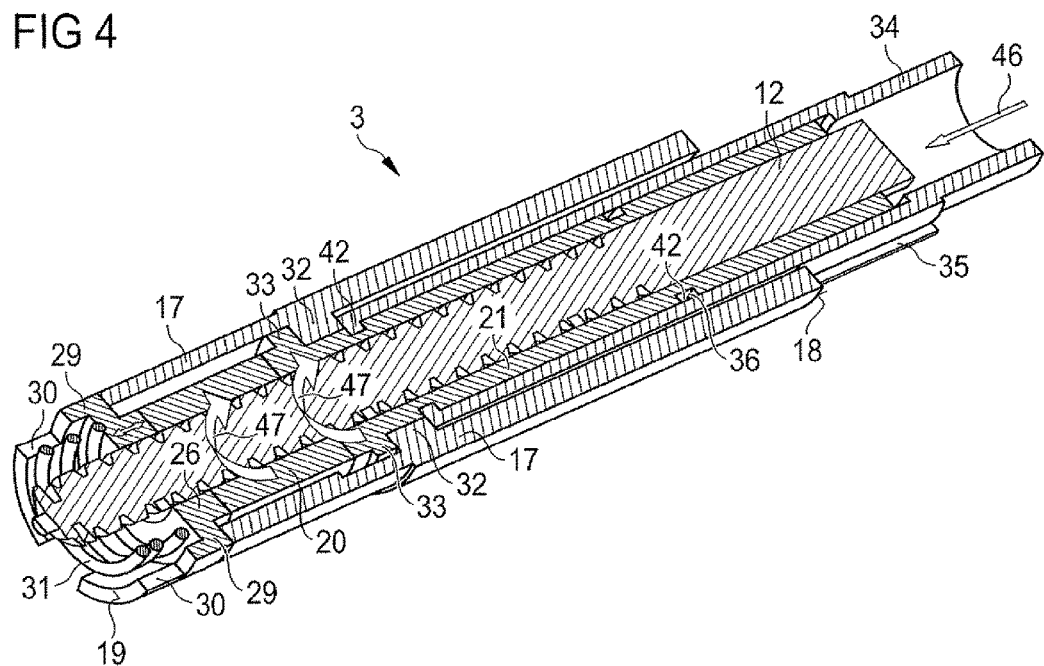
FIG. 4 schematically shows a perspective sectional view of a part of the drive mechanism according to the first embodiment with indicated movements of elements thereof during delivery of a dose.
Figure 5:
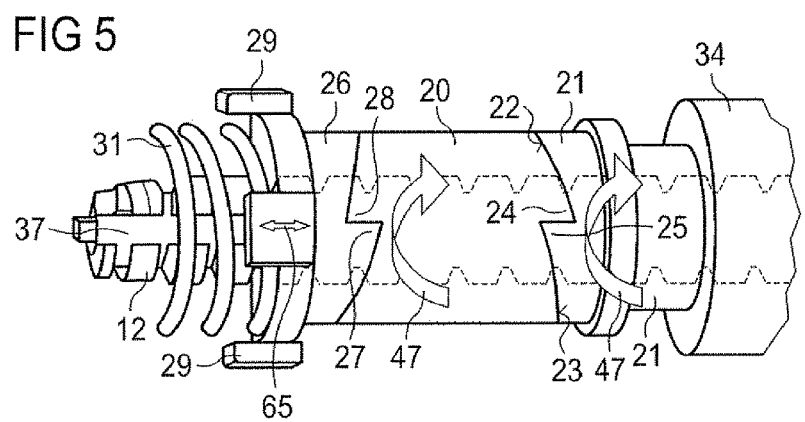
FIG. 5 schematically shows a more detailed side view of a part of FIG. 4.
Figure 6:
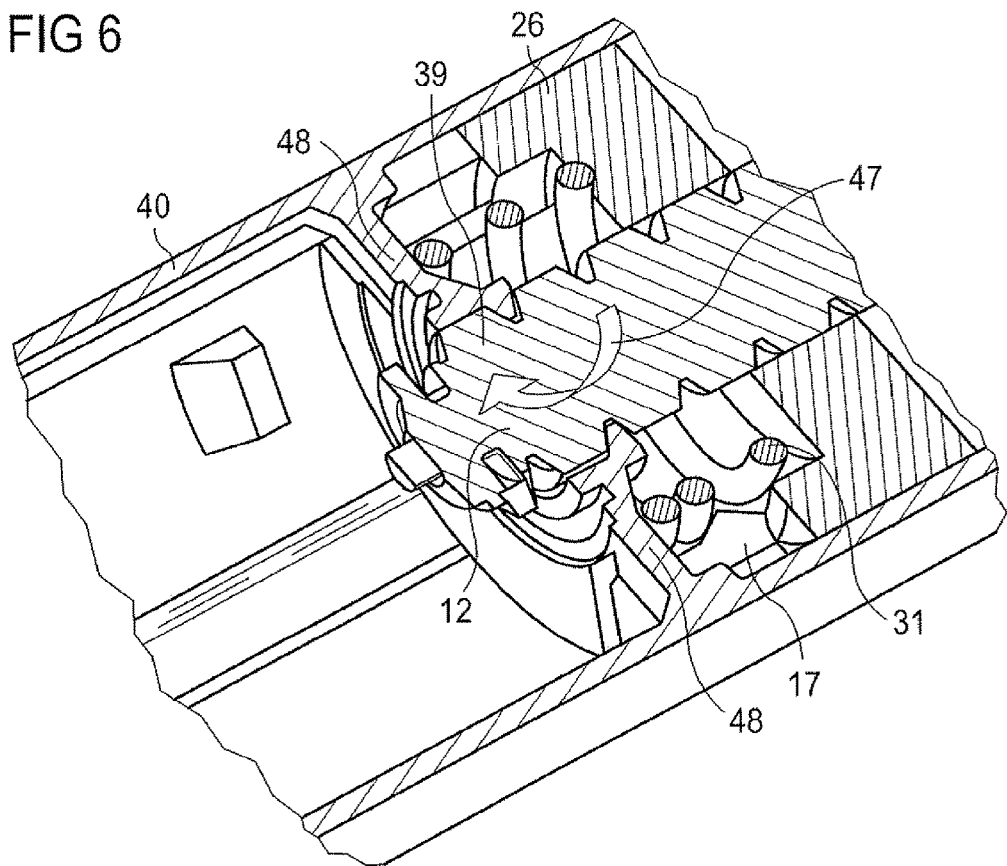
FIG. 6 schematically shows a perspective sectional view of a part of a drive mechanism that is configured in accordance with the first embodiment.
Figure 7:
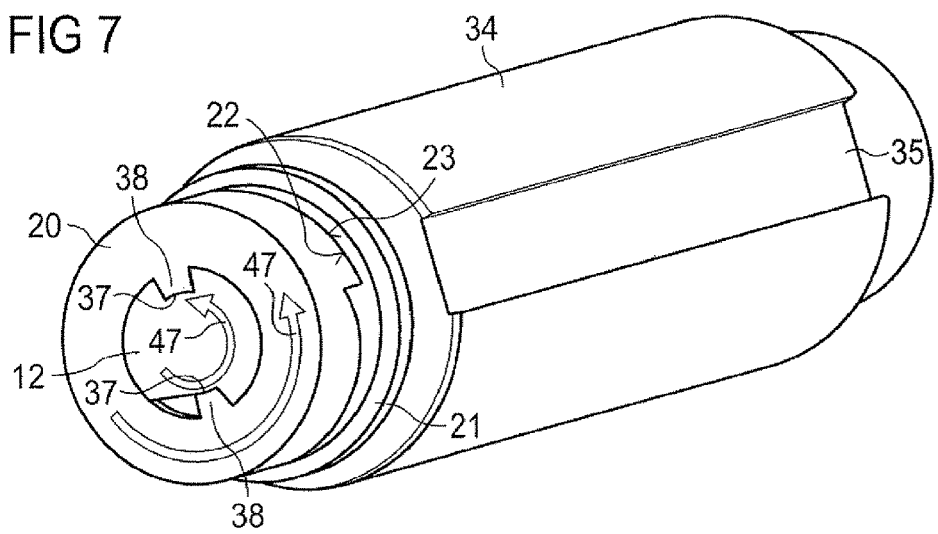
FIG. 7 schematically shows a perspective view of a part of the drive mechanism of FIG. 2 with indicated movements of elements thereof during delivery of a dose.

Turning now to FIG. 1, a medication delivery device 1 comprises a cartridge unit 2 and a drive unit 3. The cartridge unit 2 comprises a cartridge 4. Medication 5 is retained in the cartridge 4. The medication 5 is preferably liquid medication. The cartridge 4 preferably comprises a plurality of doses of the medication 5. The medication 5 may comprise insulin, heparin, or growth hormones, for example. The cartridge 4 has an outlet 6 at its distal end. Medication 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

The term "distal end" of the medication delivery device 1 or a component thereof may refer to that end of the device or the component which is closest to the dispensing end of the device 1. The term "proximal end" of the medication delivery device 1 or a component thereof may refer to that end of the device or the component which is furthest away from the dispensing end of the device, In FIG. 1, the distal end of the device 1 was assigned reference numeral 7 and the proximal end of the device was assigned reference numeral 8.

The outlet 6 may be covered by a membrane 9, which protects medication 5 against external influences during storage of the cartridge. For medication delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the medication 5 within the cartridge. The piston 10 expediently seals the interior of the cartridge 4 proximally. Movement of the piston 10 with respect to the cartridge 4 in the distal direction causes medication 5 to be dispensed from the cartridge through outlet 6 during operation of the device.

The cartridge unit 2 furthermore comprises a cartridge retaining member 11, The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit may be detached from the drive unit 3, for example in order to allow for providing for a new cartridge 4, if all of the doses of medication which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of medication may be dispensed from the cartridge in this way. The size of the delivered dose may be determined by the distance by which the piston 10 is displaced with respect to the cartridge 4 in the distal direction.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rotates and is displaced with respect to the housing, the bearing member is preferably only displaced, i.e. does not rotate. The piston rod may be bounded by the bearing member.

The drive unit 3 comprises a housing 13 which may be part of the drive mechanism. The piston rod 12 may be retained in the housing. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the medication delivery device, preferably from the drive member to the piston, for example for the purpose of discharging/dispensing, an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the medication 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of medication of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. The drive mechanism is preferably configured to not move the piston rod 12 with respect to the housing 13 when the dose part is moved in the proximal direction with respect to the housing for setting of the dose.

Embodiments of a drive mechanism which are suitable to be provided in the medication delivery device 1 as it was described above are described in more detail below.

A first embodiment of a drive mechanism which is suitable for being implemented in the medication delivery device 1 as described above is described in connection with FIGS. 2 to 9.

The drive mechanism comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements 64, for example snap-fit elements, for fixing housing part 17 to housing 13 (cf. FIG. 8).

The piston rod 12 is retained in the housing 13, preferably within housing part 17. The piston rod 12 is driven in the distal direction with respect to the housing part 17 during dose delivery.

The drive mechanism furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the medication, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to the drive member 20 by an uni-directional clutch mechanism, in particular a friction clutch mechanism. This clutch mechanism permits rotational movement of the rotation member 21 with respect to the drive member 20 when the rotation member rotates in the first direction with respect to the housing part 17. The clutch mechanism prevents rotational movement of the rotation member 21 with respect to the drive member 20, when the rotation member rotates in the second direction with respect to the housing part 17. The drive member 20 may thus follow rotational movement of the rotation member 21 in the second direction with respect to the housing part 17.

The drive member 20 is arranged to abut and/or engage the rotation member and, in particular, engages rotation member 21. The drive member 20 comprises a toothing 22 at one end, e.g. its proximal end. The rotation member comprises a toothing 23 at one end which end faces the drive member 20, e.g. its distal end. Toothing 22 comprises a plurality of teeth 24. Toothing 23 comprises a plurality of teeth 25. Teeth 24 and/or 25 may extend along the rotation axis. Toothings 22 and 23 may be configured to mate with one another.

A respective tooth of teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be disposed along the perimeter of that end of the drive member 20 which faces the rotation member 21. The teeth 25 may be disposed along the perimeter of the rotation member 21 at that end which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, the rotation member 21 may rotate with respect to the drive member 20.

The drive mechanism furthermore comprises a stop member 26. The drive member may be arranged between the stop member 26 and the rotation member 21. The stop member 26 is configured for preventing rotational movement of the drive member 20 in the first direction with respect to the housing part 17 during setting of a dose, i.e. when the rotation member rotates in the first direction. Thus, the rotation member 21 may rotate in the first direction with respect to the housing part 17, whereas the drive member 20 and the stop member 21 don't rotate.

The stop member 26 is coupled to the drive member 20 by another uni-directional clutch mechanism, in particular a friction clutch mechanism. This clutch mechanism prevents rotational movement of the drive member 20 with respect to the stop member 20 when the rotation member rotates in the first direction with respect to the housing part 17. The clutch mechanism permits rotational movement of the drive member 20 with respect to the stop member 26, when the rotation member rotates in the second direction with respect to the housing part 17.

Thus, the rotation member 21 may rotate with respect to the drive member 20 and the stop member 26 in the first direction during setting of the dose, with rotation of the drive member being prevented by its interaction with the stop member, and rotation member as well as drive member may rotate with respect to the stop member in the second direction during delivery of the dose.

The stop member may be arranged to abut and/or engage the drive member during setting of the dose and, preferably, during delivery of the dose. The stop member 26 has a toothing 27 at one end which faces the drive member, e.g. its proximal end. The teeth may be ramp-shaped. with a steep side and a less steep ramp. The teeth may be disposed azimuthally along the perimeter of the stop member.

Drive member 20 has a toothing 28 at one end which faces the stop member, e.g. its distal end. Toothings 22 and 28 of the drive member 20 are oppositely disposed. Toothing 28 may be configured in accordance with toothing 21 of the rotation member. Toothing 22 may be configured in accordance with toothing 27 of the stop member. Toothings 27 and 28, in particular the steep sides of the teeth, do cooperate, e.g. abut, for preventing rotation of the drive member 20 with respect to the housing part 17 and, in particular, with respect to the stop member 26 in the first direction.

Stop member 26 is preferably secured against rotational movement with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 5. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising drive member 20, stop member 26 and rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for medication delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member. Alternatively, the distance may be greater than the (maximum) depth of a tooth of the respective toothing.

Furthermore, the drive mechanism comprises a resilient member 31, preferably a spring member. The resilient member 31 may be biased during medication delivery operation of the drive mechanism. The resilient member may provide for a force that tends to keep the drive member 20 in engagement with the stop member 26 and/or the rotation member 21. The force may be exerted along the rotation axis. In the situation shown in FIGS. 2 to 5, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the medication. Alternatively or additionally, the resilient member 31 may keep the drive member 20 and the rotation member 26 in (permanent) mechanical contact, preferably abutment, with each other during setting and delivery of a dose of the medication.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member with the drive member and of the drive member with the stop member during setting and delivery of medication is facilitated in this way.

The rotation member 21 has an (radially) outwardly protruding member 33, for example a flange portion. The protruding member 33 is expediently provided for abutting support member 32, in particular the distal end side of support member 32.

Another support 48 (cf. FIG. 6) may be provided for providing a counterforce to the force exerted by the resilient member 31. Support 48 is arranged on that side of the drive member 20 which is remote from the rotation member 21. Support 48 is arranged on that side of the stop member 26 which is remote from the support member 32. The support 48 may be arranged to abut the resilient member 31. The support 48 may be secured against axial and rotational movement with respect to the housing part 17, with respect to the housing 13 or integrated into the housing 13, for example into (additional) housing part 40 (cf. FIG. 6).

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13.

Dose member 34 may be moved in the proximal direction and in the distal direction with respect to rotation member 21. Dose member 34 is arranged to be couplable and is preferably (permanently) coupled to rotation member 21 such that movement of the dose member, e.g. in the proximal direction with respect to the housing part 17, for setting a dose of the medication is converted into rotational movement of the rotation member in the first direction and movement of the dose member, e.g. in the proximal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 42 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 21.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

The piston rod 12 is threadedly coupled to the housing 13. The piston rod 12 may be provided with an outer thread 49, for example. The piston rod 12 may extend through and be engaged with a (part) thread in opening 39 which is provided in housing part 40, for example in support 48 (cf. FIG. 6). Housing part 40 may be formed integrally with housing part 17, may be a housing part fixed thereto or may be a housing part secured separately from housing part 17 to housing 13.

The piston rod 12 comprises an engagement track 37, preferably two oppositely disposed engagement tracks, on the outside. The (respective) engagement track 37 may interrupt thread 49. The (respective) engagement track 37 preferably extends along the axia along which the piston rod is displaceable with respect to the housing and, in particular, with respect to the drive member.

Rotational movement of the drive member 20 with respect to the housing may thus be converted into rotational movement of the piston rod 12 with respect to the housing and the rotational movement of the piston rod 12 is, on account of the threaded engagement of the piston rod and the housing (part), converted into movement of the piston rod with respect to the housing in the distal direction.

Figure 8:
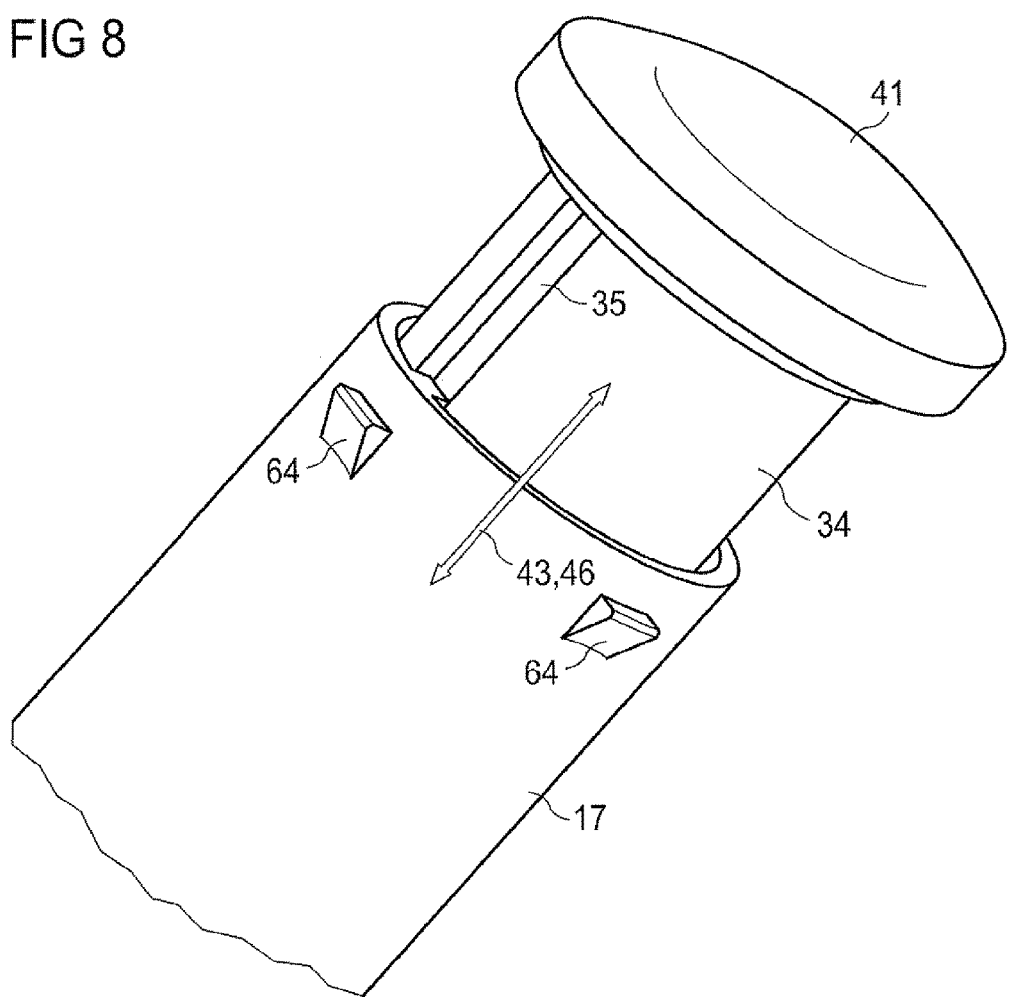
FIG. 8 schematically shows a perspective view of a part of a drive mechanism that is configured in accordance with the first embodiment.
Figure 9:
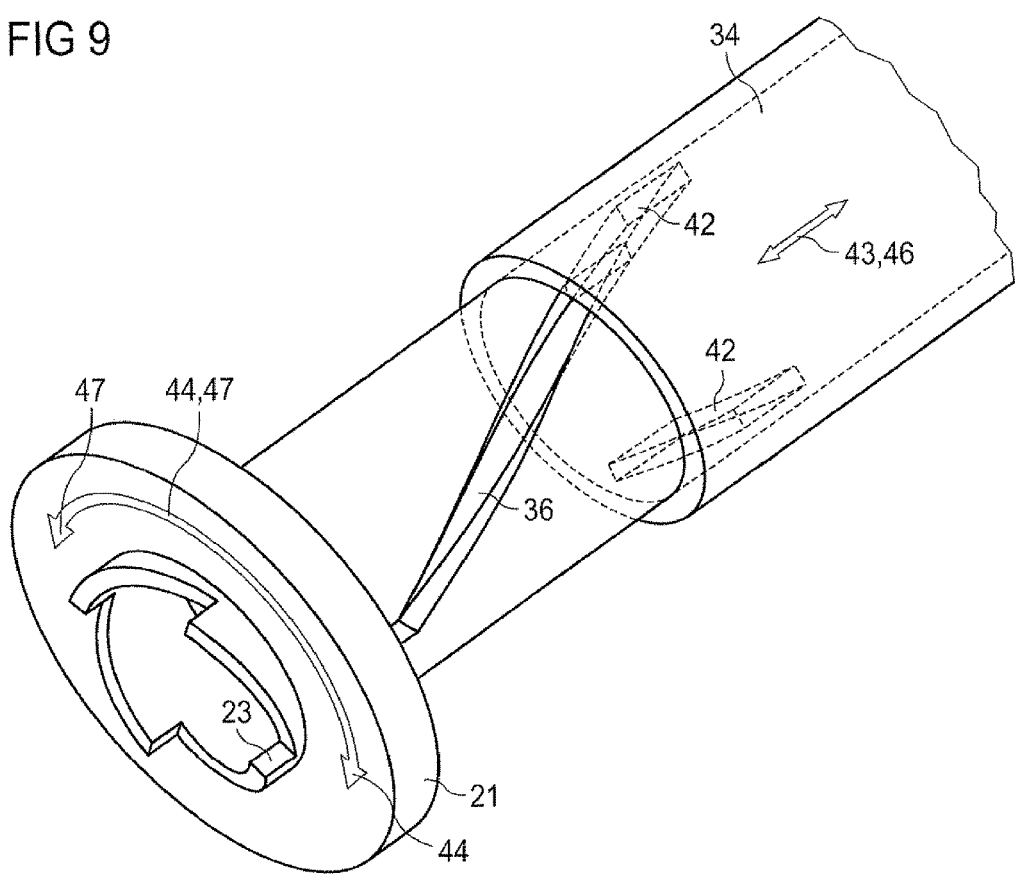
FIG. 9 schematically shows a perspective view of a part of a drive mechanism that is configured in accordance with the first embodiment.

The dose part 16 (cf. FIG. 1) may comprise a dose knob 41 (cf. FIG. 8). Dose knob 41 may be configured to be gripped by a user. Dose knob 41 may be arranged and connected to the dose member 34 at the proximal end. Dose knob and dose member may be unitary.

In the following, operation of the present drive mechanism for delivering medication from the cartridge 4 of FIG. 1 is described.

To set a dose, a user may manually move dose member 34 in the proximal direction (arrow 43) with respect to the housing part 17 (cf. FIGS. 2, 3, 8 and 9). To do so, the user may grip dose knob 41 and pull it in the proximal direction. Dose member 34 moves proximally also with respect to the rotation member 21. Proximal movement of the rotation member is prevented. by support member 32 which abuts protruding member 33 of rotation member 21. Consequently, the proximal movement of dose member 34 with respect to the housing part 17 is converted into rotational movement of the rotation member 21 in the first direction (arrow 44) with respect to the housing part 17, in particular on account of the threaded engagement of dose member 34 and rotation member 21. Thus, the rotation member 21 rotates in the first direction—counter-clockwise as seen from the proximal end of the rotation member—with respect to the housing. Rotation member 21 also rotates with respect to the drive member 20 and to the stop member 26. The drive member 20 is prevented from rotating in the first direction by interaction with the stop member 26, e.g. by interlocking of toothings 27 and 28. As the piston rod 12 is coupled to the drive member 20 and rotation in the first direction of the drive member would cause the piston rod to travel in the proximal direction, the piston rod 12 is prevented from being driven in the proximal direction by interaction of stop member 26 and drive member 20. Dose accuracy can be increased in this way.

When the rotation member 21 rotates in the first direction, the ramps of the teeth of toothing 23 of rotation member 21 slide along the ramps of the teeth of toothing 22. Thus, a tooth of the rotation member may index around the rotation axis until the tooth engages one of the next teeth of toothing 22 of drive member 20. The teeth of rotation member 21 slide along the ramps of the teeth of drive member 20. During this movement, drive member 20 and, in particular, stop member 26 are displaced along the rotation axis with respect to piston rod 12 and housing by a distance determined by, preferably equal to, the depth of a tooth of toothing 22, before a tooth of toothing 23 (totally) disengages that tooth of toothing 22. Afterwards, the tooth of the rotation member 21 engages the next tooth of toothing 22 and the force provided by resilient member 31 moves drive member 20 and, in particular, stop member 26 back along the rotation axis into the axial start position. An according movement of stop member and drive member in the distal direction and back into the proximal direction is indicated by double arrow 45 in FIGS. 2 and 3.

A tooth of the rotation member which engages the next tooth of the drive member may cause an audible and/or tactile feedback to the user.

The drive mechanism is suitable for a fixed dose device or a user settable dose device. The size of the fixed dose of medication which is to delivered or the increments in which a user-settable dose may be varied by a user are preferably determined by the distribution of the teeth of the respective toothings in the drive member, rotation member and stop member. The rotation member may be rotated over more than one teeth (dose increment) of the drive member for a user-settable dose device and over one teeth (only) for a fixed dose device. The number of teeth in the drive member 20 over which the rotation member 21 rotates during dose setting determines the size of the dose which is actually delivered. The dose member and the rotation member may be adapted to one another such that the rotation member may rotate only by one tooth for a fixed dose device and by more than one tooth for a variable dose device.

After the dose has been set, the dose part 16 and with it the dose member 34 is moved (pushed) by the user in the distal direction with respect to housing part 17 (arrow 46; cf. FIGS. 4, 5, 8 and 9). Thus, the dose member 34 is moved in the distal direction with respect to the housing part 17. The rotation member 21 accordingly rotates in the second direction, which is opposite to the first direction, with respect to the housing (arrow 47, cf. FIGS. 4 to 9). Drive member 20 follows rotational movement of the rotation member in the second direction. Rotational movement of the drive member 20 in the second direction is converted into rotational movement of the piston rod 12 in the second direction, which movement, in turn, is converted into movement of the piston rod 12 in the distal direction. Accordingly, the piston 10 of FIG. 1 may be displaced in the distal direction with respect to the cartridge 4 and a dose of medication 5 is dispensed from the cartridge the amount of which corresponds to the previously set dose.

During dose delivery, toothings 22 and 23 interlock and ramps of the teeth of toothing 28 of the drive member 20 slide along ramps of the teeth of toothing 27 of stop member 26. This movement is similarly as described above for the relative rotational movement of rotation member and drive member with opposite rotation direction. The stop member 26 is thereby displaced in the distal direction with respect to the drive member 20 by a distance corresponding to the depth of a tooth of toothing 27 in stop member 26. Resilient member 28 forces the stop member 26 back into the axial starting position, when the next tooth of toothing 28 is engaged by the respective tooth of toothing 27 (double arrow 65).

A tooth of the drive member which engages the next tooth of the stop member may cause an audible and/or tactile feedback to the user.

Figure 10:
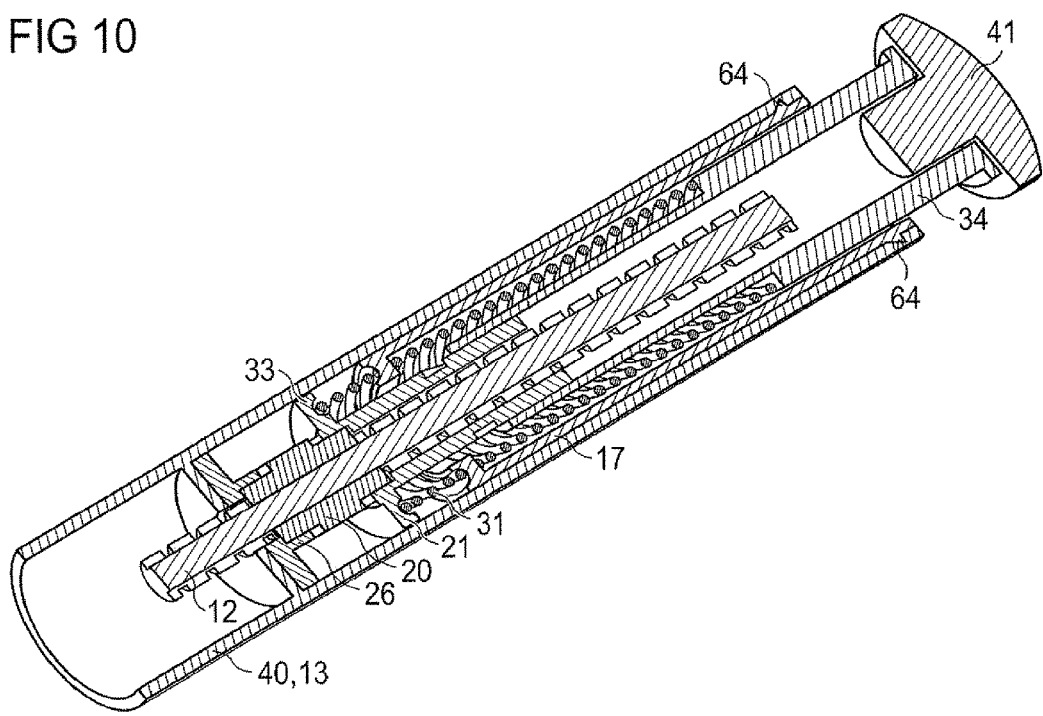
FIG. 10 schematically shows an oblique sectional view of a drive mechanism according to a second embodiment.
Figure 11:
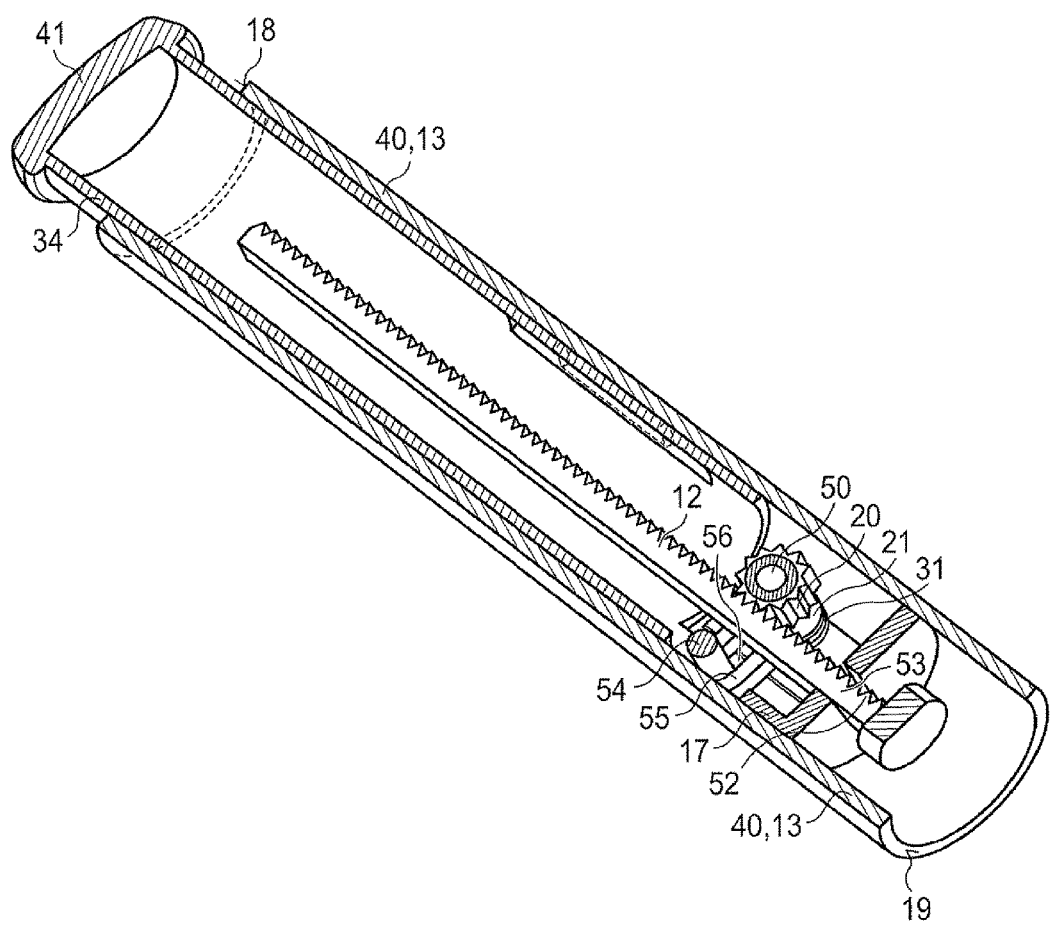
FIG. 11 schematically shows an oblique sectional view of a drive mechanism according to a third embodiment.
Figure 12:
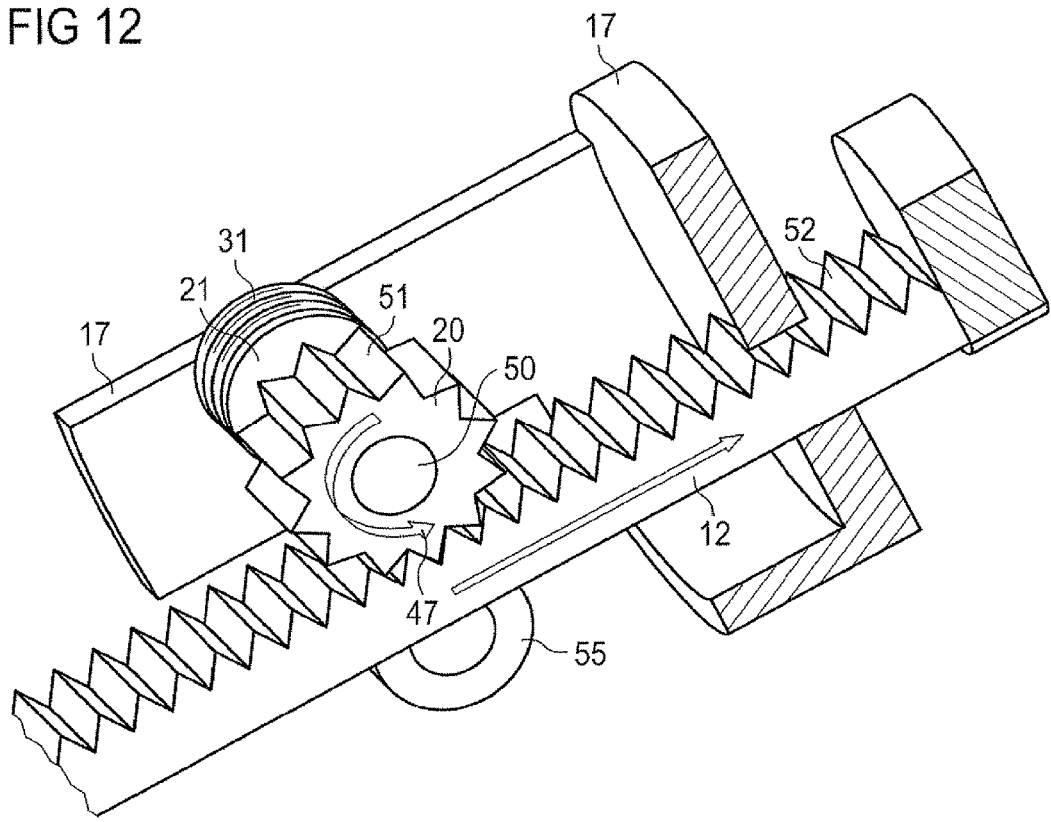
FIG. 12 schematically shows an oblique sectional view of a part of the drive mechanism of FIG. 11.
Figure 13:
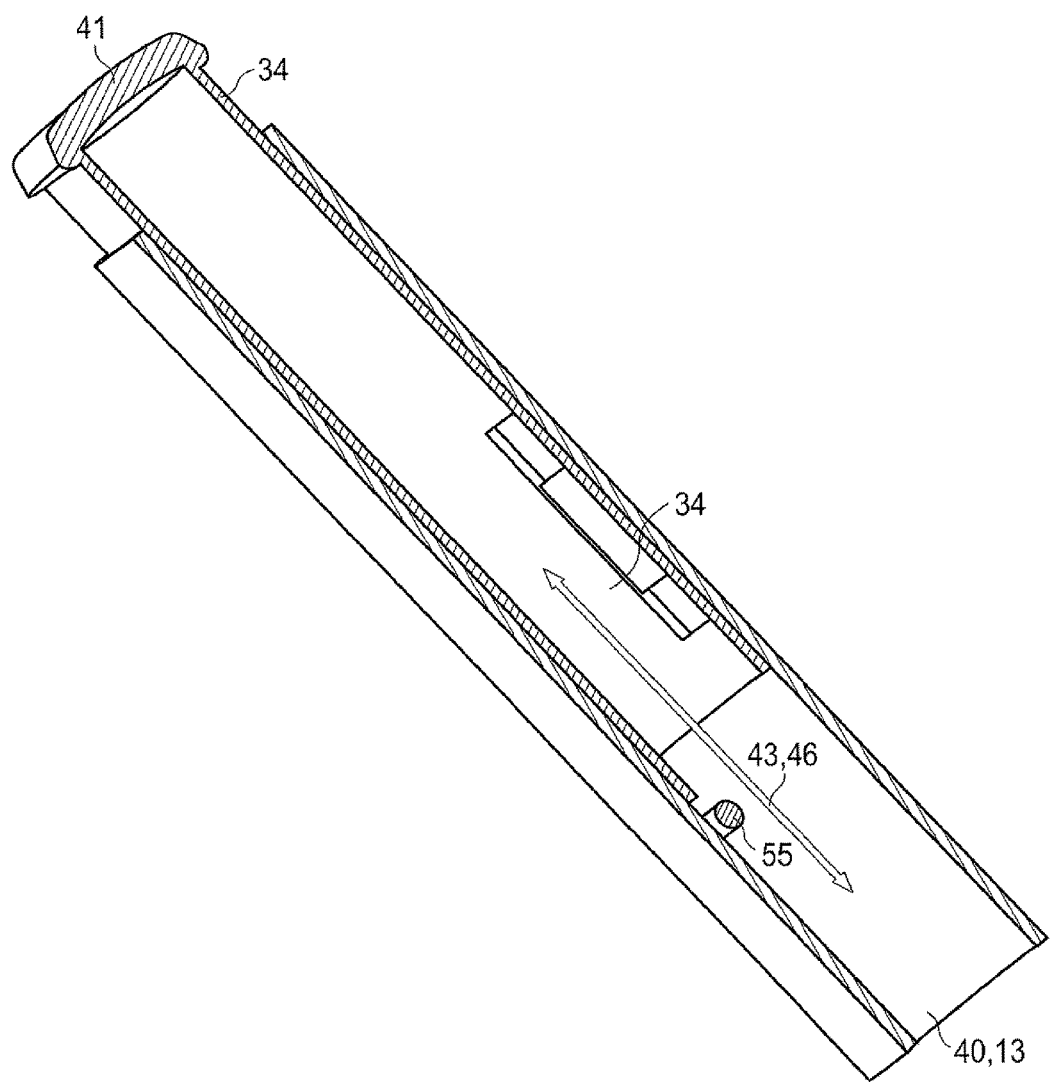
FIG. 13 schematically shows an oblique sectional view of a part of the drive mechanism of FIG. 11.
Figure 14:
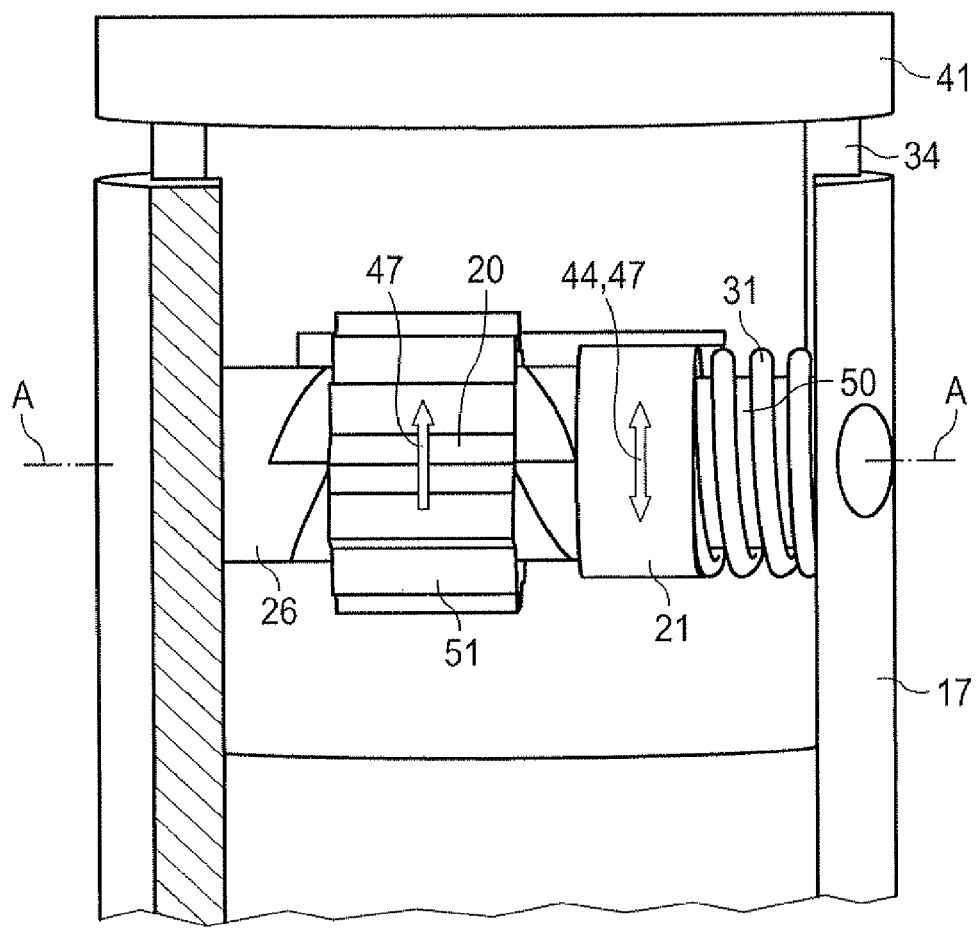
FIG. 14 schematically shows an oblique sectional view of a part of the drive mechanism of FIG. 11.

FIG. 10 schematically shows an oblique sectional view of a second embodiment of a drive mechanism. This drive mechanism essentially corresponds to the one described in conjunction with FIGS. 2. to 9. In contrast thereto, the stop member 26 is secured against rotational movement and displacement with respect to the housing (13, 17, 40). Stop member 26 may be integrated in housing part 40 or 17 or an insert thereof. Housing part 40 may be housing 13, for example, Housing part 17 may be inserted and fixed within housing 13. Fixing elements 64 may engage corresponding elements in the housing for fixing the housing part 17 to housing part 40.

In order to compensate for the relative axial displacement between rotation member 21, drive member 20 and stop member 26, when the respective parts rotate with respect to one another, the rotation member 21 is movable with respect to the housing. In order to keep stop member 26 and rotation member 21 in, preferably permanent, abutment with drive member 20 during medication delivery operation of the drive mechanism, resilient member 31 exerts a force on the rotation member 21, preferably on protruding member 33 thereof which presses rotation member and drive member 20 towards stop member 26. Resilient member 31 may be arranged at that side of the drive member which faces away from the stop member, e.g. its proximal side. Resilient member may abut the proximal face of protruding member 33. Support member 32 can thus be dispensed with. The distal end face of housing part 17 may act as an abutment surface for the resilient member 31.

However, when the elements are arranged as shown in FIG. 10, axial movement of the rotation member, which may occur correspondingly to the axial movement of the stop member in the previous embodiment, may be transferred to the dose part 16 and thereby to the user. This movement of an external part might be irritating for a user.

FIGS. 11 to 15 schematically show a third embodiment of a drive mechanism which is suitable for being provided in the medication delivery device 1 as described in conjunction with FIG. 1.

The drive mechanism essentially corresponds to the one described in connection with the previous embodiments. In contrast thereto, the drive member 20 and, in particular, the rotation member 21 are rotatable around a rotation axis which runs obliquely with respect to the axis along which the piston rod 12 is displaced (displacement axis). The rotation axis (cf. axis A in FIG. 14) may run transversally, in particular perpendicularly, with respect to the displacement axis and, in particular, with respect to a main direction of extent of the piston rod 12.

Drive member 20 and rotation member 21 may be retained by an axis member 50, which may extend through rotation member 21 and drive member 20. Axis A may run along axis member 50. Axis member may secure drive member and rotation member against displacement with respect to the housing. Stop member 26 may be integrated into housing 13. Of course, stop member 26 may also be embodied as a separate element. Axis member 50 may extend through stop member 26.

Drive member 20 comprises an outer toothing 51. Teeth of the outer toothing 51 may extend radially away from rotation axis A. Drive member may be a toothed gear sleeve. The piston rod 12 is expediently provided with an outer toothing 52. The outer toothing 52 of piston rod 12 and the outer toothing 51 of the drive member 20 are arranged to engage one another. The outer toothing 52 of piston rod 12 and the outer toothing 51 of the drive member 20 may be permanently engaged. When the drive member 20 and the rotation member 21 rotate together in the second direction with respect to the housing 13, the piston rod 12 is also displaced in the distal direction with respect to the housing. The piston rod does not rotate while it is displaced in the distal direction with respect to the housing.

The piston rod 12 may be supported against deviation in the radial direction with respect to the displacement axis, for example by means of housing part 17 through an opening 53 in which the piston rod may extend.

In contrast to the previously described embodiments, the dose member 34 and the rotation member 21 are not threadedly engaged. Rather, rotation member 21 and dose member 34 are connected/coupled to one another via a lever mechanism. The lever mechanism is adapted to convert movement of the dose member 34 with respect to the housing in the proximal direction into rotational movement of the rotation member in the first direction with respect to the housing and movement of the dose member 34 with respect to the housing in the distal direction into rotational movement of the rotation member in the second direction with respect to the housing.

Drive member 20 is prevented to rotate during setting of the dose on account of the stop member 26 preventing rotational movement of the drive member in the first direction.

The lever mechanism may comprise a lever 55. Lever 55 is preferably secured against rotational movement with respect to rotation member 21 and preferably against (simultaneous) translational movement with respect to rotation member 21. Preferably, lever 55 is formed unitary with rotation member 21. Lever 55 is pivotally around the rotation axis in the first direction during dose setting and in the second direction during dose delivery.

Dose member 34 may, preferably at its distal end, comprise an engagement member 54, e.g, a pin, for engagement with the lever 55. Engagement member 54 may engage the lever 55, in particular an opening 56, preferably an elongate opening 56 within lever 55.

Stop member 26 prevents rotational movement of the drive member in the first direction during dose setting as described previously.

Figure 16:
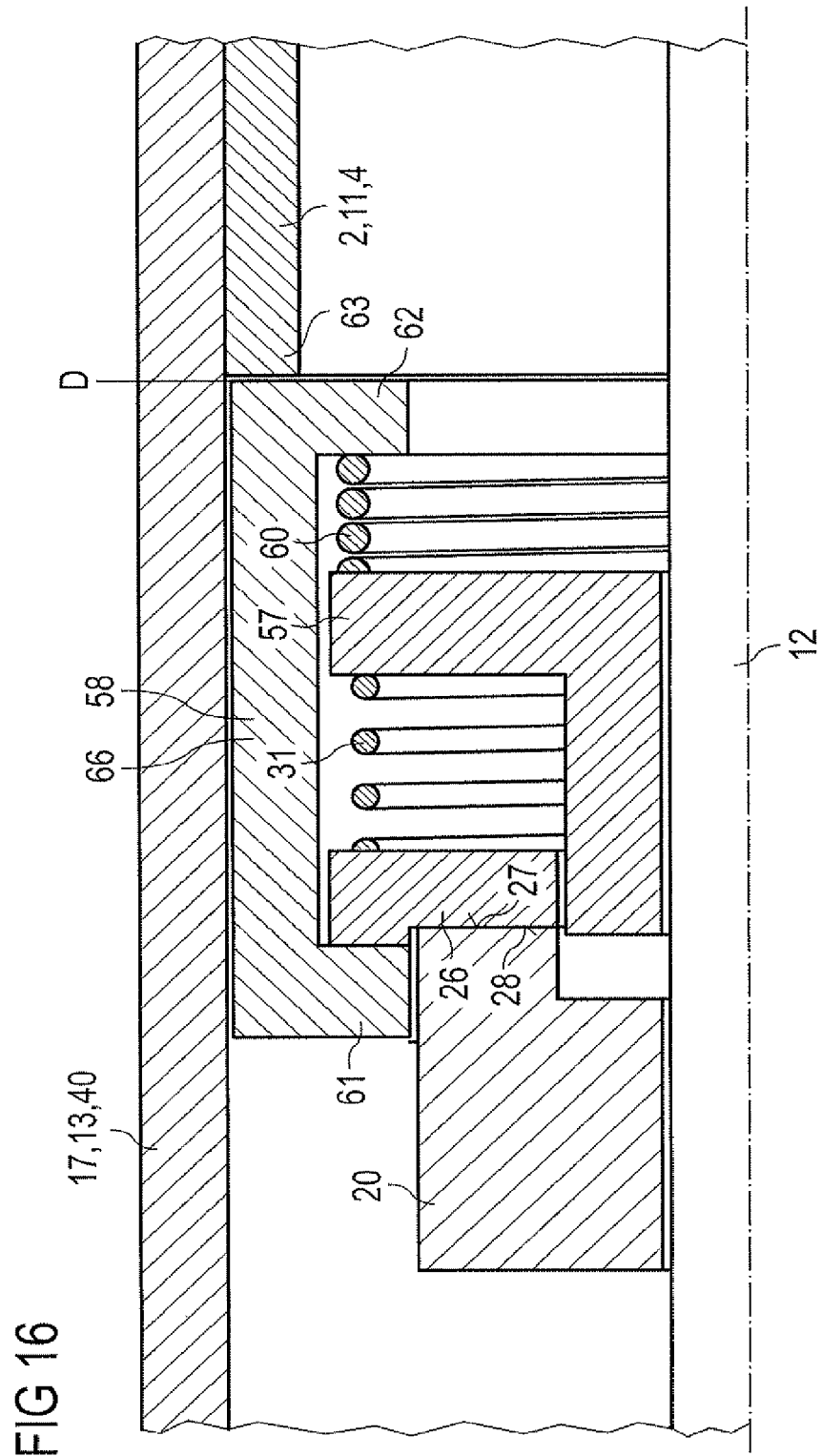
FIG. 16 shows a schematic sectional view of a part of a resettable drive mechanism according to an embodiment in delivery position.
Figure 17:
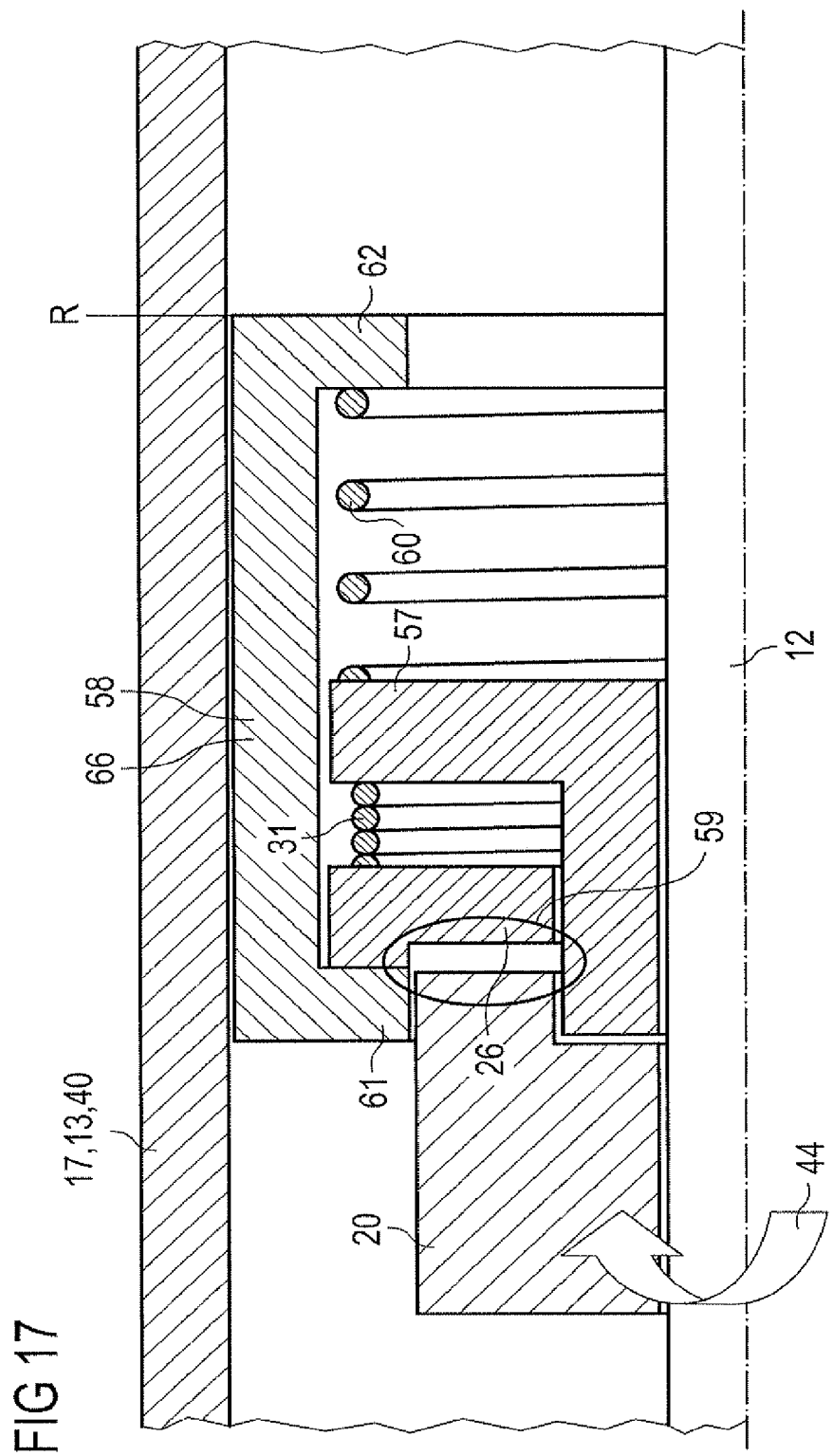
FIG. 17 shows the resettable drive mechanism of FIG. 16 in reset position.

FIG. 16 shows a schematic sectional view of a part of a resettable drive mechanism according to an embodiment in a delivery state. FIG. 17 shows the resettable drive mechanism of FIG. 16 in a reset state.

The drive mechanism may correspond to the one described in conjunction with FIGS. 2 to 9. However, a reset mechanism for a drive mechanism as it is described in more detail below may also be provided for in the remaining drive mechanisms as described above.

Figure 15:
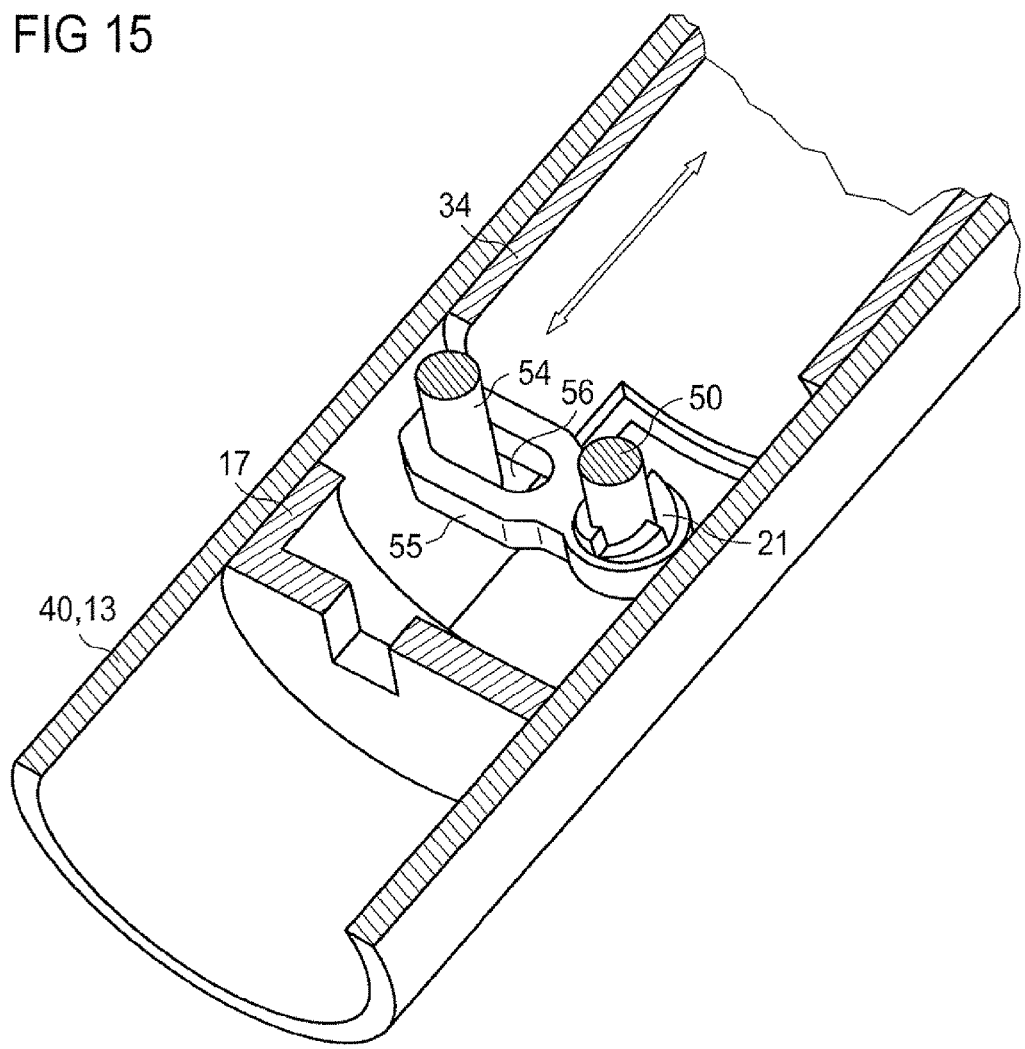
FIG. 15 schematically shows an oblique sectional view of a part of the drive mechanism of FIG. 11.

The drive mechanism described in conjunction with FIGS. 15 and 16 is a resettable drive mechanism. For this purpose, the drive mechanism comprises a reset mechanism. The reset mechanism may be switched between a reset position and a delivery position.

In contrast to the drive mechanism described in conjunction with the previous figures, the rotation member 21 is not shown in FIGS. 16 and 17. However, a rotation member may nevertheless be provided. FIGS. 16 and 17 only show a half of a section through the drive mechanism. The additional cut was made along piston rod 12.

As shown in FIG. 16, in the delivery state, drive member 20 and stop member 26 are engaged with one another such that rotational movement of the drive member 20 with respect to housing 13 in the first direction is prevented and rotation of the drive member 20 in the second direction, opposite to the first direction, is allowed. Toothings 27 and 28 may be provided for this purpose as described further above. Resilient member 31 exerts a force acting in axial direction on stop member 26, said force tending to keep the stop member and the drive member engaged. Resilient member 31 may be arranged to keep stop member in engagement and, in particular, in abutment with drive member 20 in the delivery state. The (biased) resilient member 31 may be supported by and, preferably, bear against bearing member 57. Bearing member may be support 48 of FIG. 6, for example. Bearing member 57 is expediently secured against rotational movement and displacement with respect to housing 13.

Rotation of the drive member 20 in the second direction may cause the piston rod 12 to be displaced in the distal direction with respect to housing 13. The piston rod 13 may rotate and translate in the distal direction with respect to the housing for dose delivery as described in conjunction with FIGS. 2 to 10. Alternatively, the piston rod may be moved in the distal direction with pure translatory movement (not explicitly shown, cf. a drive mechanism according to FIGS. 11 to 15). The drive member 20 may engage the piston rod 12. The drive member 20 may be splined to the piston rod 12. Preferably, there is no relative rotational movement possible between piston rod 12 and drive member 20. Also, the drive member 20 preferably cannot be rotated in the first direction on account of the (permanent) interlocking of the drive member 20 and the stop member 26 when the reset mechanism is in the delivery state.

Thus, when the drive mechanism is in the delivery state, movement of the piston rod 12 in the proximal direction with respect to housing 13 to a starting position is prevented, because the stop member 26 prevents rotation of the drive member 20 in the first direction and the drive member has to be rotated in the first direction, if the piston rod 12 was to be moved in the proximal direction with respect to the housing 13 into the starting position.

However, after a cartridge 4 has been emptied, i.e. after a distal end position of the piston 10 and, in particular, of the piston rod 12 has been reached, the piston rod has to be moved in the proximal direction back into a proximal starting position in order to allow the drive mechanism to be reused. Expediently, the drive mechanism is configured to be switchable from the delivery state to a reset state. In the reset state, the piston rod 12 may be moved in the proximal direction with respect to the housing, for example by a user screwing and/or pushing the piston rod 12 in the proximal direction.

The drive mechanism comprises a clutch member 58. Clutch member 58 is movable with respect to housing 13, preferably displaceable with respect to the housing, between a delivery position D and a reset position R. The clutch member 58 may be moved back and forth between the delivery position and the reset position. The reset position may be arranged in the distal direction as seen from the delivery position.

The clutch member 58 may be a sleeve. Piston rod 12 may extend through clutch member.

In the delivery position, drive member 20 and stop member 26 are engaged. In the reset position, drive member 20 and stop member 26 are disengaged (cf. the encircled region 59 in FIG. 17). Thus, when the clutch member 58 is in the reset position, the drive member may be rotated in the first direction with respect to the housing 13 without the stop member 26 preventing the rotation. Consequently, the piston rod 12 may be moved in the proximal direction, e.g. by rotation with respect to the housing and on account of a threaded engagement to the housing, due to the drive member 20 and the stop member 26 being disengaged.

The clutch member 58 may comprise a protrusion 61. Protrusion 61 may protrude radially and preferably inwardly from a base portion 66 of the clutch member 58. The base portion may extend in the axial direction. Protrusion 61 may be arranged to move the drive member 20 and the stop member 26 out of engagement when the clutch member is moved towards reset position R. Protrusion 61 may be provided at or near the proximal end of the clutch member 58. A distal end face of protrusion 61 of clutch member 58 may be arranged to couple to and preferably to abut a proximal face of stop member 26.

The reset mechanism furthermore comprises a clutch resilient member 60, for example a clutch spring member, like a coil spring and/or a compression spring, for example.

The clutch member 58 may extend along drive member 20, stop member 26, resilient member 31, bearing member 57 and/or clutch resilient member 60. The clutch member 58 may be rigid. The clutch member 58 may have a constant length.

Clutch resilient member 60 may be biased when the clutch member 58 is in the delivery position. Biased clutch resilient member may exert a force on the clutch member that tends to move the clutch member in the reset position. Clutch resilient member 60 may bear on bearing member 57, in particular on a distal face thereof.

Clutch member 58 may comprise a (additional) protrusion 62. Protrusion 62 may protrude radially and preferably inwardly from the base portion 66 of the clutch member 58. Protrusion 62 may be arranged in the region of the distal end of the clutch member 58. Protrusion 62 may be arranged to be abuttable by and is preferably abutted by clutch resilient member 60. Clutch resilient member 60 may be supported by and, in particular, bear on a proximal face of protrusion 62.

The clutch resilient member 60 is arranged to exert a force on the clutch member 58 which force tends to move the clutch member 58 in the reset position R. When the drive mechanism is in the delivery state, this force is counteracted by a clutch stop member 63. Accordingly, in the delivery state, clutch member 58 may be held in the delivery position by the clutch stop member 63.

In the delivery state, clutch stop member 63 is preferably secured against displacement with respect to the housing 13. Clutch stop member 63 may be arranged to abut clutch member 58. A proximal end face of the clutch stop member 63 may abut a distal end face of the clutch member 58 in the delivery state.

For resetting the device, the clutch stop member 63 may be moved, for example removed, so as to allow the clutch member to move into the reset position. Thereupon, biased clutch resilient member 60 which exerts the force, which is no longer compensated by clutch stop member, on clutch member 58. The force automatically tends to move clutch member 58 in the reset position R. The clutch member 58 may abut stop member 26. Stop member 26 may tend to follow movement of the clutch member towards the reset position R.

In order to get into reset position the force exerted by e resilient member 31 on the stop member 26, which force tends to hold drive member 20 and stop member 26 in engagement, has to be overcome. Thus, the force moving the clutch member 58 towards the reset position 58 has to be greater than the force exerted by the resilient member 31. The force for moving and, in particular, holding the clutch member 58 in reset position R may be provided for by clutch resilient member 60. It is expedient for the resilient member 31 and the clutch resilient member 60 to be embodied as a spring member, respectively. Clutch resilient member 60, in this case, preferably has a spring strength greater than the one of resilient member 31 in order to overcome the force exerted by resilient member 31.

The clutch stop member 63 is expediently formed in the cartridge unit, for example, by the cartridge 4 or the cartridge retaining member 11. Thus, if the cartridge unit is detached from the housing 13 for replacing an empty cartridge, the clutch member 58 is moved, preferably automatically, towards and into the reset position and preferably held in the reset position.

The distance by which the clutch member 58 moves with respect to the housing 13 when moving from delivery position into reset position is preferably chosen to be great enough to disengage toothings 27 and 28.

The clutch member 58 is expediently secured to the drive mechanism in order to avoid the clutch member falling out of the housing. For this purpose, the clutch member may abut a proximal face of the stop member 26.

As shown in FIG. 17, when the clutch member 58 is in reset position R, the drive mechanism is in the reset state and the piston rod 12 may be moved in the proximal direction with respect to the housing from a distal end position back into a proximal starting position. When a new cartridge 4 is attached to the housing 13, after the piston rod 12 was moved back into starting position, clutch member 58 may be moved into the distal direction back into delivery position together with the cartridge 4 and, if present, the cartridge retaining member 11, thereby moving drive member 20 and stop member 26 again into engagement.

Accordingly, the medication delivery device may be reused. As an element of the cartridge unit like cartridge 4 or cartridge retaining member 11 may serve as the clutch stop member 63, the reset mechanism may automatically and, in particular (purely) mechanically, decouple stop member 26 and drive member 20, when the cartridge unit 2 is detached from the drive unit 3 (cf. FIG. 1). Thus, the only action required by a user is to move, e.g. screw and/or push, the piston rod 12 back into the starting position before a new cartridge unit 2 may be attached to the drive unit 3. The drive mechanism is thus easily reusable.

The reset mechanism described herein above may be implemented easily and requires only a small amount of additional parts such as compared to the corresponding non-resettable drive mechanism. In particular, such as compared to the first embodiment, only two additional parts—clutch member and clutch resilient member—are required for the automatic reset mechanism.

As the reset mechanism may be an automatic one, no external action is required for disengaging stop member and drive member. Thus, the clutch member may be retained in the housing and, in particular, inaccessible from the outside.

Of course, the reset mechanism may be implemented as a manual, non-automatic mechanism. It is expedient, in this case, to configure the movement of the clutch member to be externally actuable.

In contrast to the situation depicted in FIGS. 16 and 17, the clutch member 58 may be (partly) arranged outside of the housing. The housing may be provided with one or more openings through which the clutch member may extend from the outside to the inside of the housing. This is particularly expedient for a non-automatic reset mechanism.

With the (resettable) drive mechanisms described herein above a good dose accuracy may be achieved. The drive mechanisms are particularly suitable for dispensing doses of the medication from and including 1 IU up to and including 30 IU, preferably from and including 3 IU up to and including 20 IU. Also, doses of 30 IU or more or 1 IU or less may be dispensed by means of the described drive mechanisms. However, doses of from and including 1 IU up to and including 30 IU are particularly suitable. For example, if a device described in conjunction with FIGS. 1 to 10, in which the piston rod rotates during displacement, was to be designed for doses less than 1 IU, the thread of the piston rod should have a low pitch and/or the number of teeth of the respective toothing of drive member and rotation member should be increased. Of course, the production costs may increase on account of the finer segmentation of the toothings and the lower pitch thread. In order to provide for a device configured to deliver doses greater than 30 IU, e.g. 50 IU or greater, the thread in the piston rod should have a higher pitch. Consequently, small deviations from a predetermined course of the thread result in major absolute deviations from the desired dose. Thus, the risk of a reduction in dose accuracy may be increased. In addition, the risk of self-locking of a threaded engagement may be increased.

A diameter of the (outer) housing of the medication delivery device may be less than or equal to 20 mm, preferably less than or equal to 16 mm, particularly preferably less than or equal to 14 mm.

A first aspect of the invention provides a drive mechanism for a predication delivery device (1), comprising:

a housing (13, 17, 40) having a proximal end and a distal end, a rotation member (21) which is adapted to be rotated in a first direction with respect to the housing during setting of a dose of a medication (5) and to be rotated in a second direction with respect to the housing during delivery of the dose, the second direction being opposite to the first direction, a piston rod (12) which is adapted to be displaced in a distal direction with respect to the housing for delivering the dose, a drive member (20) which follows rotational movement of the rotation member in the second direction during delivery of the dose, and a stop member (26) which prevents rotational movement of the drive member with respect to the housing in the first direction during setting of the dose, wherein the rotational movement of the drive member in the second direction is converted into movement of the piston rod in the distal direction with respect to the housing.

A second aspect provides a drive mechanism according to the first aspect, wherein the drive mechanism comprises a dose member (16, 34, 41) which is moveable with respect to the housing (13, 17, 40) during setting and delivery of the dose, and wherein movement of the dose member with respect to the housing is converted into rotational movement of the rotation member with respect to the housing.

A third aspect provides a drive mechanism according to the second aspect, wherein the dose member (16, 34, 41) is secured against rotational movement with respect to the housing (13, 17, 40).

A fourth aspect provides a drive mechanism according to any one of the first through third aspects, wherein the drive member (20) and the rotation member (21) are rotatable about a common rotation axis.

A fifth aspect provides a drive mechanism according to the fourth aspect, wherein the piston rod (12) is displaced in the distal direction with respect to the housing (13, 17, 40) along the rotation axis.

A sixth aspect provides a drive mechanism according to the fourth aspect, wherein the piston rod (12) is displaced in the distal direction with respect to the housing (13, 17, 40) transversally with respect to the rotation axis.

A seventh aspect provides a drive mechanism according to any one of the second through sixth aspects, wherein the dose member (16, 34, 41) and the rotation member (21) are threadedly engaged.

An eighth aspect provides a drive mechanism according to any of the second through sixth aspects, wherein the dose member (16, 34, 41) and the rotation member (21) are coupled to one another by a lever (55), the lever being pivotally around the rotation axis during movement of the dose member for setting and delivery of the dose.

A ninth aspect provides a drive mechanism according to any one of the first through eighth aspects, wherein the drive member (20) abuts stop member (26) and rotation member (21) during movement of the rotation member for setting and delivery of the dose.

A tenth aspect provides a drive mechanism according to any one of the first through ninth aspects, wherein the rotation member (21) and the stop member (26) are held in abutment with the drive member (20) by a force provided by a spring member (31) during setting and delivery of the dose.

An eleventh aspect provides a drive mechanism according to any one of the first through tenth aspects, wherein the drive member (20) and the rotation member (21) are coupled to one another by a first uni-directional friction clutch mechanism, which is configured to permit relative rotational movement between rotation member and drive member during rotation of the rotation member in the first direction for setting of the dose and to prevent relative rotational movement of rotation member and drive member during rotation of the rotation member in the second direction for delivery of the dose.

A twelfth aspect provides a drive mechanism according to any one of the first through eleventh aspects, wherein the drive member (20) and the stop member (26) are coupled to one another by a second uni-directional friction clutch mechanism, which is configured to prevent relative rotational movement between stop member and drive member during rotation of the rotation member (21) in the first direction for setting of the dose and to permit relative rotational movement of stop member and drive member during rotation of the rotation member in the second. direction for delivery of the dose.

A thirteenth aspect provides a drive mechanism according to any one of the first through twelfth aspects, wherein the stop member (26) is secured against rotational movement with respect to the housing (13, 17, 40).

A fourteenth aspect provides a drive mechanism according to any one of the first through thirteenth aspects, wherein the stop member (26) is moveable in an axial direction with respect to the housing (13, 17, 40).

A fifteenth aspect provides a medication delivery device (1) comprising the drive mechanism according to any one of the first through fourteenth aspects, and a cartridge (4), the cartridge holding a plurality of doses of the medication (5).

Of course, the invention is not restricted by the embodiments described above.

The invention claimed is:

1. A resettable drive mechanism for a medication delivery device, comprising:
   a housing with a proximal end and a distal end;
   a drive member rotatable in a second direction with respect to the housing for delivering a dose of a medication;
   a piston rod which is splined to the drive member, where rotation of the drive member in the second direction causes displacement of the piston rod in the distal direction with respect to the housing;
   a stop member adapted to prevent rotation of the drive member with respect to the housing in a first direction opposite to the second direction when the stop member engages the drive member; and
   a clutch member movable with respect to the housing between a delivery position and a reset position,
   wherein when the clutch member is in the delivery position, the stop member and the drive member are engaged and the drive member is prevented from rotating in the first direction with respect to the housing and when the clutch member is in the reset position, the drive member and the stop member are disengaged, the drive member is rotatable in the first direction with respect to the housing and the piston rod is movable in the proximal direction with respect to the housing.

2. The resettable drive mechanism of claim 1, wherein the piston rod is threadedly engaged with the housing.

3. The resettable drive mechanism of claim 1, wherein there is no relative rotation between the piston rod and the drive member.

4. The resettable drive mechanism of claim 1, wherein the clutch member is rigid and has a constant length.

5. The resettable drive mechanism of claim 1, wherein the clutch member is secured in the drive mechanism in order to prevent the clutch member from falling out of the housing.

6. The resettable drive mechanism of claim 1, wherein a diameter of the housing is less than or equal to 20 mm.

7. The resettable drive mechanism of claim 1 further comprising a dose member which is movable in the proximal direction with respect to the housing for setting the dose of medication and in the distal direction with respect to the housing for delivering the set dose, wherein movement of the dose member for delivering the set dose is converted into rotational movement of a rotation member with respect to the housing in the second direction.

8. The resettable drive mechanism of claim 7, wherein the rotation member is operatively connected to the drive member to rotate the drive member in the second direction.

9. A medication delivery device, comprising the resettable drive mechanism of claim 1, wherein the medication delivery device further comprises a clutch stop member, wherein the clutch stop member is secured to the housing when the clutch member is in the delivery position, and wherein the clutch stop member is removable from the housing in order to allow that the clutch member moves from the delivery position into the reset position.

* * * * *